United States Patent [19]

Molnar et al.

[11] Patent Number: 4,457,304
[45] Date of Patent: Jul. 3, 1984

[54] SELF-REGULATING INFANT VENTILATOR

[75] Inventors: Hugo Molnar, Palm Springs, Calif.; David L. Robbins, St. Paul, Minn.

[73] Assignee: Minnesota Mining and Manufacturing Company, Saint Paul, Minn.

[21] Appl. No.: 327,553

[22] Filed: Dec. 4, 1981

[51] Int. Cl.³ ............................................. A61M 16/00
[52] U.S. Cl. ........................... 128/204.25; 128/205.24
[58] Field of Search ...................... 128/200.11, 203.12, 128/203.14, 204.18, 204.19, 204.21, 204.23, 204.26, 204.24, 204.25, 205.13, 205.19, 205.23, 205.24

[56] References Cited

U.S. PATENT DOCUMENTS

| | | | |
|---|---|---|---|
| 3,842,828 | 10/1974 | Bird | 128/204.25 |
| 3,985,131 | 10/1976 | Buck et al. | 128/204.23 |
| 4,256,101 | 3/1981 | Ellestad | 128/204.23 |

OTHER PUBLICATIONS

McPherson, *Respiratory Therapy Equipment*, 1977–pp. 222 and 367.

McPherson, *Respiratory Therapy Equipment*, 1981–p. 486.

Primary Examiner—Henry J. Recla
Attorney, Agent, or Firm—Donald M. Sell; James A. Smith; William L. Huebsch

[57] ABSTRACT

An infant ventilator of the type that switches between an inspiration phase during which gas under pressure is applied through a mouthpiece to cause involuntary inspiration of an infant to which the mouthpiece is coupled, and an expiration phase during which the infant is allowed to exhale or voluntarily inhale through the mouthpiece while gas flows past the mouthpiece. The gas delivery system in the ventilator is interconnected so as to regulate the gas pressure at the mouthpiece during the expiration phase to generally atmospheric pressure (in the absence of operator selected PEEP) for any flow rate of gas past the mouthpiece in the expiration phase in the range of about 0 to 25 liters per minute as selected by a flow control valve without the need for further manual adjustments.

3 Claims, 3 Drawing Figures

SELF-REGULATING INFANT VENTILATOR

Technical Field

This invention relates to infant ventilators of the type that switch between an inspiration phase during which gas under pressure is applied through a mouthpiece to cause involuntary inspiration of an infant to which the mouthpiece is coupled, and an expiration phase during which the infant is allowed to exhale or voluntarily inhale through the mouthpiece while gas flows past the mouthpiece; and in one important aspect to the gas delivery system in such ventilators that regulates the gas pressure at the mouthpiece during the expiration phase.

Background Art

Gas flow past the mouthpiece during the expiration phase in an infant ventilator of the type described above is important to both sweep exhaled gases from the mouthpiece to ensure that the infant will not inhale his own exhaled gases, since the mouthpiece holds a large volume of gas compared to the volume of an infant's breath; and to provide gas which the infant may voluntarily inhale during the expiratory phase, since it is difficult to design a ventilator that can be switched to an inspiration phase by an infant's weak attempts to inhale.

Typically in the type of ventilator described above, a flexible hose through which the gas flows past the mouthpiece continues to an outlet end of the hose spaced from the mouthpiece at which outlet end is positioned an outlet valve movable via control means for the ventilator between (1) a closed position blocking the outlet end of the hose so that gas pressure at the mouthpiece will increase sufficiently to cause involuntary inspiration of an infant to which the mouthpiece is coupled (the inspiration phase of the ventilator), and (2) an open position so that gas will flow past the mouthpiece and through the outlet end of the hose to the atmosphere (the expiration phase of the ventilator). The resistance of the hose to the flow of gas between the mouthpiece and its outlet end during the expiration phase of the ventilator, however, will normally cause a pressure slightly above atmospheric pressure at the mouthpiece, which pressure (called PEEP by those skilled in the art) is sometimes undesirable. Thus while one prior art gas delivery system currently in use simply accepts a pressure above atmospheric pressure at its mouthpiece during its expiration phase; other prior art gas delivery systems currently in use include means for reducing the gas pressure at the mouthpiece when the outlet valve is open, which means includes a venturi at the outlet end of the hose that exhausts gas supplied to the venturi through the open end of the hose while the throat of the venturi reduces gas pressure within the hose around the venturi, and thus also in the hose at the mouthpiece.

In one such prior art gas delivery system the rate of gas flow through the venturi and the rate of gas flow past the mouthpiece in the inspiration phase are manually regulated by an operator via separate valves on the ventilator. With that gas delivery system an operator can inadvertently set too high a rate of flow through the venturi so that the pressure at the mouthpiece goes below atmospheric pressure, which is potentially dangerous for an infant to which the mouthpiece is coupled.

In another such prior art gas delivery system the rate of gas flow past the mouthpiece in the inspiration phase is manually adjustable, however no manually-adjustable means is provided to control the rate of gas flow through the venturi. Instead the size of the venturi and the flow rate through the venturi are selected so that there would normally always be a pressure below atmospheric pressure at the mouthpiece even for the maximum rate of gas flow past the mouthpiece selected when the outlet valve is fully open; and in the expiration phase the outlet valve is opened only a limited amount via a manually-adjustable circuit to partially defeat the effect of the venturi and thus produce atmospheric pressure at the mouthpiece. Such a gas delivery system can also be inadvertently adjusted so that a below atmospheric pressure is produced at the mouthpiece, however; flow variations in the gas delivery system can cause changes in the pressure at the mouthpiece; and the gas delivery system uses a relatively large amount of gas compared to the other gas delivery systems described above.

Disclosure of Invention

The present invention provides a gas delivery system for a ventilator generally of the type described above that can be controlled by a single flow control valve to set a desired rate of gas flow past a mouthpiece in the range of about 0 to 25 liters of gas during the expiration phase of the ventilator, which can produce pressure at the mouthpiece in the range of 0 to 1 centimeter of water over that range of gas flowing past the mouthpiece, and which does so without using the large amount of gas required for the gas delivery system described in the preceding paragraph.

According to the present invention there is provided an infant ventilator comprising a gas delivery system including (1) a supply portion having a first end adapted to be coupled to a source of gas under pressure, a second end, a manually-adjusted flow control valve between the first and second ends for regulating the rate of gas flow through the ventilator; (2) a patient delivery portion having an inlet end coupled to the second end of the supply portion, an opposite outlet end, a mouthpiece between the inlet and outlet ends adapted to be coupled to the breathing passageways of an infant, means for restricting the flow of gas through the patient delivery portion to a flow rate in the range of about 0 to 25 liters per minute and for generating back-pressure at the second end of the supply portion, an outlet valve at the outlet end of the hose movable between a closed position so that gas pressure at the mouthpiece will increase sufficiently to cause involuntary inspiration of an infant to which the mouthpiece is coupled, and an open position at which gas can flow past the mouthpiece to allow exhalation of the infant, remove any exhaled gases from the mouthpiece, and afford voluntary inhalation of the infant; and (3) a mouthpiece pressure-regulating portion comprising a first end coupled to the second end of the supply portion and an opposite second end, a venturi coupled to the second end of the pressure-regulating portion and positioned in the patient supply portion between the mouthpiece and the outlet valve, and a restriction between the first and second ends of the pressure-regulating portion.

Surprisingly the size of the restriction in the mouthpiece pressure-regulating portion of such a gas delivery system can be selected so that for any setting of the flow control valve to produce a desired amount of flow past the mouthpiece from within the indicated range of about 0 to 25 liters per minute when the outlet valve is fully opened, gas will also flow through the venturi at a rate that will cause generally the same pressure at the mouthpiece (e.g., within about 1 centimeter of water), which pressure may be atmospheric or some pressure slightly above atmospheric pressure. While this same pressure would not be maintained at the mouthpiece for rates of gas flow substantially above the indicated range, the fact that it will be maintained for flow rates within the indicated range affords a simplified safe infant ventilator with the advantages indicated above.

Additionally, the ventilator according to the present invention may have the additional feature of safety means activated by a pressure at the mouthpiece above a predetermined level for activating an alarm, exhausting the patient delivery portion of the gas delivery system, and interrupting the flow of gas through the supply portion of that system, which safety means provides significantly more safety for an infant coupled to the mouthpiece than the known types of high pressure relief valves normally used in prior art gas delivery systems.

Brief Description of Drawing

The present invention will be further described with reference to the accompanying drawing wherein like reference numerals refer to like parts in the several views and wherein.

Description of Preferred Embodiment

Figure 1:
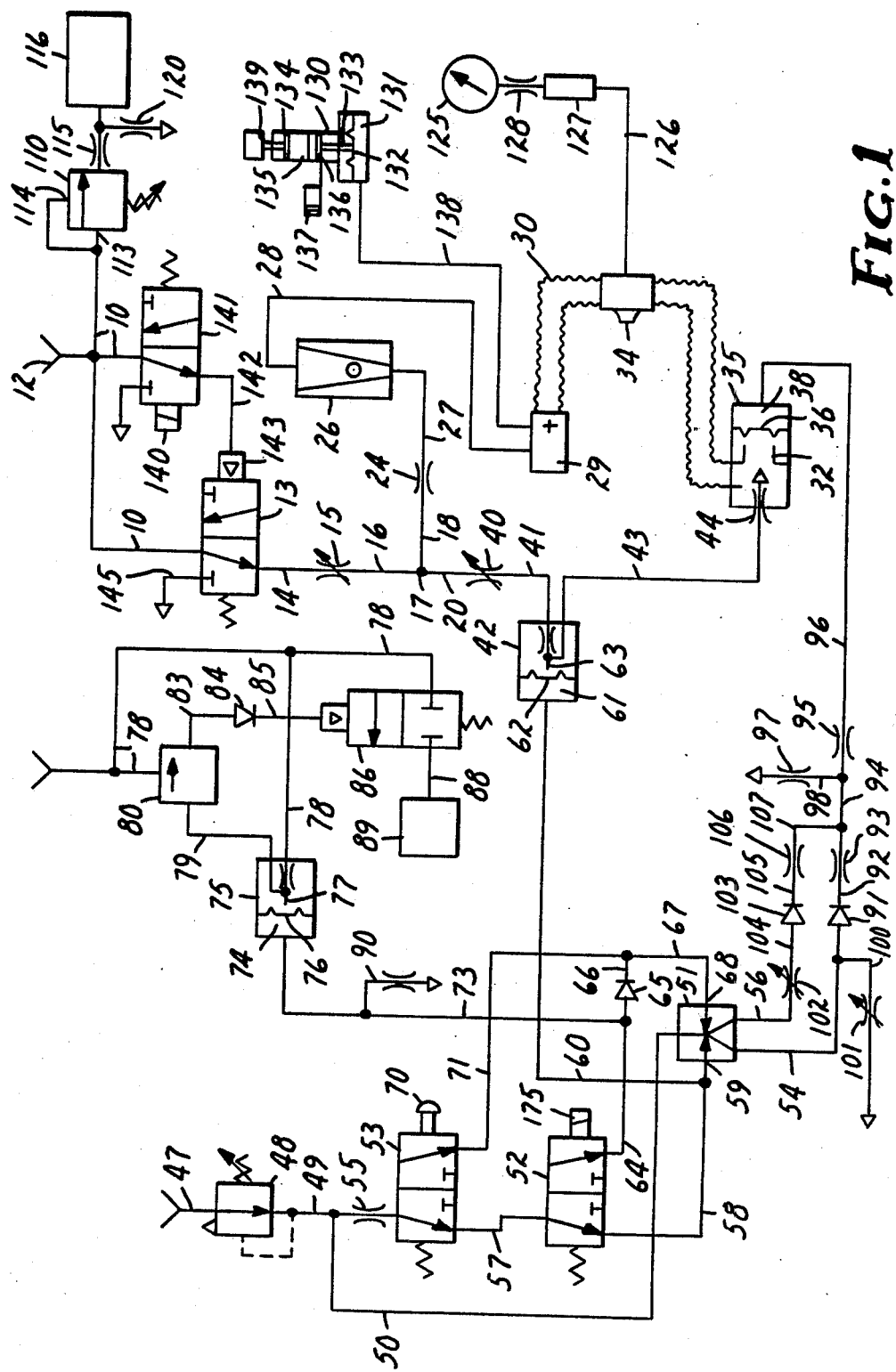
FIG. 1 is a schematic view of a gas delivery system in an infant ventilator according to the present invention.

Referring now to FIG. 1 there is shown a schematic diagram of a gas delivery system in an infant ventilator according to the present invention.

Generally, the gas delivery system includes a supply portion comprising a gas supply network 10 having an inlet end 12 defining a first end for the supply portion adapted to be coupled to a source of gas under pressure (e.g., a mixture of air and oxygen) and coupled at its opposite end to an inlet port of a gas-operated spring return spool valve 13 that provides a portion of an overpressure safety system to be explained later, a line 14 connecting a first outlet port of the spool valve 13 to a manually-adjustable flow control needle valve 15, and a line 16 connecting the valve 15 to a junction 17 with lines 18 and 20, which junction 17 defines a second end for the supply portion of the gas delivery system. The gas delivery system also includes a patient delivery portion including the line 18 and having an inlet end defined by the end of the line 18 coupled to the junction 17. The end of the line 18 opposite the junction 17 is coupled to a restriction 24 that limits gas flow through the patient delivery portion to a rate in the range of from about 0 to 25 liters per minute; which rate may be set by manual adjustment of the flow control valve 15 and will be indicated on a Thorp tube 26 coupled to the restriction 24 by a line 27. A line 28 connects the outlet of the Thorp tube 26 to the inlet end 29 of a flexible hose 30. The hose 30 has an outlet end 32 opposite its inlet end 29, a mouthpiece 34 between its ends 29 and 32 adapted to be coupled to the breathing passageways of an infant. An outlet valve 35 is positioned at the outlet end 32 of the hose 30 and includes a diaphragm 36 adapted to be moved between (1) a closed position (not shown) to which it can be urged by air pressure in a chamber 38 coupled to a switching system later to be explained, at which closed position the diaphragm 36 closes the outlet end 32 of the hose 30 to cause gas pressure at the mouthpiece 34 to increase sufficiently to cause involuntary inspiration of an infant to which the mouthpiece 34 is coupled (the inspiration phase of the ventilator); and (2) a normally open position (illustrated in FIG. 1) at which the diaphragm 36 is spaced from the outlet end 32 of the hose 30 and gas can flow past the mouthpiece 34 and out the outlet end 32 of the hose 30 to the atmosphere (the expiration phase of the ventilator). A mouthpiece pressure-regulating portion of the gas supply system is provided by the line 20 which has an end coupled at the junction 17 that defines a first end for the mouthpiece pressure-regulating portion. The line 20 is coupled to a restriction or needle valve 40 intended to be adjusted once when the gas delivery system is assembled and to then remain fixed except for possible recalibration by a serviceman. A line 41 couples the restriction 40 to a diaphragm amplifier 42 that provides a part of the switching system later to be explained, which in turn is coupled by a line 43 to a venturi 44 in the hose 30 at its outlet end 32. The venturi 44 includes a small jet (i.e., preferably about 0.04 centimeter or 0.016 inch in diameter) directed so that it will discharge through the outlet end 32 of the hose 30 and so that the throat of the venturi 44 will reduce the gas pressure at the outlet end 32 of the hose, and thus reduce the gas pressure at the mouthpiece 34 to essentially the same predetermined pressure during the expiration phase of the ventilator, which reduced pressure at the mouthpiece 34 will be about atmospheric or slightly above atmospheric pressure for any rate of gas flow set by the valve 15.

The portion of the gas delivery system that switches the outlet valve 35 between its open and closed position by releasing or applying air pressure from the chamber 38, and thus respectively causes the expiration and inspiration phases of the ventilator, is supplid by oxygen from an external source through a line 47. The line 47 is coupled to a pressure regulator 48 from which oxygen at a reduced pressure (e.g., 8 psi) is supplied by lines 49 and 50 to a digital amplifier 51 that may be switched via an electronically-operated spring spool valve 52 operated by an electronic control circuit for the ventilator (FIG. 2) or by a manually-operable spring return spool valve 53 into either a line 54 to cause the chamber 38 of the outlet valve 35 to be pressurized and close the outlet and 32 of the hose 30, or into a line 56 to allow the pressure in the chamber 38 to escape and the outlet valve 35 to open via circuitry that will later be explained.

Oxygen is supplied to the inlet port of the manually-operable spool valve 53 past a restriction 55 in the line 49 that reduces the oxygen pressure (e.g., to about 2 to 3 psi), from which valve 53 oxygen is supplied to the inlet port of the electrically-operated spool valve 52 by a line 57 when the manually-operated spool valve 53 is in its normal position (illustrated in FIG. 1).

When the electrically-operated spool valve 52 is also in its normal position (as illustrated in FIG. 1), oxygen will pass through it and a line 58 coupled between its first outlet port and a first pilot port 59 of the digital amplifier 51 which causes the oxygen passing through the line 50 to pass into the line 56 which will allow pressure capable of closing the diaphragm 36 in the chamber 38 to escape so that the outlet valve 35 will be open and gas will flow past the mouthpiece 34 and out the outlet opening 32. Also, oxygen from the line 58 will pass via a line 60 to a chamber 61 in the diaphragm amplifier 42 so that a diaphragm 62 therein will close the open end of a tube 63 and cause gas from the line 41 to pass into the line 43 to the venturi 44 rather than escape through the open end of the tube 63 and a vent in the diaphragm amplifier 42 as happens when its chamber 61 is not pressurized during the inspiration phase of the ventilator. Thus while the gas flows out of the outlet end 32 of the hose 30 during the expiration phase of the ventilator, the venturi 44 is activated to reduce the gas pressure in the hose 30 at the mouthpiece 34.

When the electronically-activated spool valve 52 is activated via the electronic circuit shown in FIG. 2, oxygen from the line 57 will pass out its second outlet port through a line 64, a one-way valve 65, and lines 66 and 67 to a second pilot port 68 of the digital amplifier 51 so that oxygen from the line 50 will pass into the line 54, the chamber 38 is pressurized, the outlet valve 35 is closed, and gas in the hose 30 is pressurized at the mouthpiece 34.

Alternatively, the manually-actuatable spool valve 53 can be activated by manual pressing of a knob 70 on the valve 53. When this is done, the oxygen supply to the electronically-actuated spool valve 52 will be blocked, and oxygen entering the inlet port of the manually-activatable spool valve 53 will pass out a second outlet port, through a line 71 and the line 67 to the second pilot port 68 of the digital amplifier 51 so that gas in the hose 30 will be pressurized as previously described. Thus the ventilator can be manually switched to its inspiration phase via the manually-activatable spool valve 53 at any time this is desired.

Circuitry is also provided for ensuring that the ventilator is not held in its inspiration phase for more than a predetermined length of time by activation of the electronically-activated spool valve 52 due to failure of the electronic control circuit or otherwise. A line 73 is coupled to the line 64 and receives oxygen pressure from the line 64 to pressurize a chamber 74 in a diaphragm amplifier 75 when the spool valve 52 is activated. Pressure in the chamber 74 moves a diaphragm 76 in the diaphragm amplifier 75 into engagement with the open end of a tube 77 so that air from an air supply network 78 will pass through a line 79 into a time delay device 80. If the chamber 74 thus remains pressurized for longer than the predetermined time period (e.g., 3.5 seconds), the time delay device 80 will connect air from the air supply network 78 to a line 83, cause it to pass through a one-way valve 84 and line 85 into the pilot pot of an air-operated spring return poppet valve 86 so that the poppet in the valve 86 shifts to couple air from the air supply network 78 through a line 88 to a normally open switch 89 that will activate an alarm in the form of a horn 184 and a light emitting diode 189 (FIG. 2). The one-way valve 84 will retain air pressure at the pilot port of the air-operated spool valve 86, so that the alarm cannot be deactivated except by a serviceman when the defect is corrected. If the electrically-activated spool valve 52 does not maintain the ventilator in the inhalation phase for the predetermined time period (as will normally be the case), after the electronically-operated spool valve 52 is deactivated air pressure in the chamber 74 will bleed off through the line 73 and a restricted open line 90.

The circuitry that couples the outlet line 54 from the digital amplifier 51 to the outlet valve 35 and supplies oxygen pressure to the chamber 38 to close the outlet valve 32 and cause the inspiration phase for the ventilator comprises a one-way valve 91, line 92, restriction 93, line 94, restriction 95 and line 96. The restrictions 93 and 95, a restriction 106 coupled to the line 94 by a line 107 and a restriction 97 open to the atmosphere and coupled to the line 94 by a line 98 have been selected to produce an inspiration pressure buildup and decay pattern designated a "modified shark-fin" in the industry, which pattern is believed to provide benefits to the infant being ventilated. A line 100 coupled between the line 54 and a manually-variable restriction or needle valve 101 having an outlet open to the atmosphere provides means to limit the amount of pressure that will be developed in the hose 30 to thereby limit the maximum gas pressure at the mouthpiece 34. As the valve 101 is opened it will allow more of the oxygen from the digital amplifier 51 to escape that would otherwise pressurize the chamber 38 in the outlet valve 32, so that pressure within the hose 30 can cause gas to escape to the atmosphere past the diaphragm 36 and thereby limit the gas pressure in the hose 30.

The circuitry that couples the outlet line 56 from the digital amplifier 51 to the outlet valve 35 and allows air pressure in the chamber 38 to escape so that the outlet valve 35 may open and cause the expiration phase for the ventilator comprises a manually-adjustable needle valve 102 coupled to a one-way valve 103 by a line 104, a line 105, the restriction 106, the line 107, the line 94, the restriction 95 and the line 96. The needle valve 102 is manually-adjustable so that it can either restrict flow of oxygen through the line 54 to an amount less than the amount that can escape to the atmosphere via the restriction 97 so that the outlet valve 35 will be fully open during the expiration phase, or it can pass a sufficient amount of oxygen so that the chamber 38 will be partially pressurized and the diaphragm 36 partially closed. Such partial closing of the diaphragm 36 will partially defeat the effect of the venturi 44 and cause a slight increase in the hose pressure at the mouthpiece 34 (PEEP), which may be desirable for some infants being ventilated.

The ventilator includes an alarm system that indicates if the pressure in the gas supply network 10 falls below a predetermined level. A spring biased normally open poppet valve 110 has both its inlet port and its pilot port coupled to the gas supply network 10 via lines 113 and 114 respectively so that gas pressure above a predetermined minimum holds the valve 110 closed. If gas pressure should fall below a predetermined level (e.g., 38 psi) a spring in the poppet valve 110 will overcome the gas pressure at it pilot port, cause the poppet valve 110 to open and gas to flow through the restricted line 115 to close a normally open gas-operated electrical switch 116 which will activate an alarm in the form of the horn 184 and a light-emitting diode 188 via the electronic circuit (FIG. 2). Gas will then also flow to the atmosphere through a restricted line 120 which serves to release gas pressure at the switch 116 and allow it to again open when the poppet valve 110 again closes upon gas pressure in the network 10 being restored to above the predetermined level.

A manometer 125 (e.g., reading from −10 to +80 cm $H_2O$) is provided for reading the pressure at the mouthpiece 34. The mouthpiece 34 is coupled to the manometer 125 via a flexible line 126, a quick disconnect coupling 127 that facilitates removal of the tube 126 with the hose 30, and a line 128 that is restricted to damp the reaction of the manometer 125 during pressure changes at the mouthpiece 34.

The overpressure safety system provided in the ventilator produces an alarm when a pressure above a predetermined maximum pressure (e.g. in the range of 30 to 80 cm $H_2O$) occurs in the hose 30. That system includes an actuator 130 having a chamber 131 that will be pressurized by gas pressure at the inlet end of the hose 30 via a line 138. As pressure in the chamber 131 increases, a diaphragm 132 will deflect and move an axially-slidable assembly within actuator 130 including a shaft 133 connected to the diaphragm 132 so that an outer steel plate 134 of the assembly mounted on the shaft 133 moves away from the force field of a permanent magnet 135 fixed within a housing of the actuator 130 (which force field can hold the outer plate 134 adjacent the magnet 135 over range of movement of the shaft 133 in generally a normal first position for the assembly), and simultaneously moves a second inner steel plate 136 spaced from the magnet 135 into the force field of the magnet 135 on the side of the magnet 135 opposite the outer plate 134. The space relationship between the magnet 135 and the outer plate 134 is adjustable via threaded engagement of the outer plate 134 and a knob 139 fixed to the outer plate 134 with the shaft 133 so that at the predetermined pressure (selected via rotation of the knob 139 to move the outer plate 134 toward the magnet 135 for higher maximum pressure, and away from the magnet 135 for lower maximum pressure), the slideable assembly is moved sufficiently that the attraction between the inner plate 136 and magnet 135 overcomes the attraction between the outer plate 134 and magnet 135, which causes the slideable assembly to move suddenly to a second alarm position with the inner plate 136 against the magnet 135. Upon such movement, the inner plate 136 will engage and close a normally open switch 137 and connect a voltage coupled to the switch 137 to a solenoid 140 of an electrically-operated spring return spool valve 141 via an electric line (FIG. 2) and activate an alarm in the form of the horn 184 and a light-emitting diode 186. Such activation of the valve 141 will cause gas from the supply network 10 normally blocked by the valve 141 to flow through the valve 141 and a line 142 to pressurize the pilot port 143 of the air-operated spring return spool valve 13. Such pressure will actuate the spool valve 13, block the connection between the gas supply network 10 and the gas delivery system and allow pressure in the hose 30 to escape via the lines 28, 27 and 16 through an outlet port 145 of the valve 13 so that the high pressure in the hose 30 will no longer be present at the mouthpiece 34. After the problem causing the overpressure in the hose 30 has been corrected, the overpressure safety system can be re-set to its original position by pressing the knob 139 toward the body of the activator 130 to return the axially-slideable assembly to its normal first position.

Referring now to FIG. 2 there is illustrated the electronic control circuit for the infant ventilator that activates and deactivates the spool valve 52 to respectively cause the inspiration and expiration phases for the ventilator, and which provides several alarms and/or signal lights in response to several functions or malfunctions of the ventilator.

The circuit includes a square wave-generating portion enclosed by a dotted line 150 that is manually adjustable via a rotary potentiometer 151 calibrated in inspiration frequencies of from 0 to 75 inspirations per minute. The portion 150 generates a square wave having a frequency that is a high multiple of the frequency set at the potentiometer 151, which frequency is transmitted via a line 152 to a frequency divider portion 153 of the control circuit which produces a square wave on a line 154 that has either the same frequency as the frequency set on the rotary potentiometer 151 if a rocker switch 155 is set at a 1X position to connect a line 156 with the line 154; or that has a frequency that is two times the frequency set on the rotary potentiometer 151 if the rocker switch 155 is set at a 2X position to connect a line 157 with the line 154.

The line 154 transmits the square wave to a pulse width shaping portion of the circuit enclosed by a dotted line 160, which portion 160 produces a series of pulses at the same frequency as the square wave on the line 154, each of which pulses is 0.2 seconds in duration. This series of pulses is transmitted via a line 161 to a portion of the circuit enclosed by a dotted line 162, the function of which will later be explained; and just at the end of each pulse on the line 161, the pulse width shaping portion 160 transmits a much shorter pulse along a line 165 to a portion of the circuit enclosed by a dotted line 167 which determines the time duration for each inspiration phase of the ventilator.

The portion 167 tha determines the time duration for each inspiration phase of the ventilator includes a rotary binary coding switch 170 calibrated for time durations of between 1 to 30 tenths of a second, which coding switch 170 may be manually set for any one of the calibrated time durations and will in response code the portion 167 of the circuitry to produce a series of signals of the selected time duration at the frequency of the pulses on the line 165. The portion 167 will then transmit that series of signals along a line 173 to a portion 174 of the circuitry that can activate a solenoid 175 on the spool valve 52 via lines 176 and 177 to cause the inspiration phases in response to the signals.

The signal along the line 173 is also transmitted via a line 179 coupled to the line 173 to the portion of the circuitry enclosed by the dotted line 162 that ensures that the frequency selected via the potentiometer 151 and rocker switch 155 and the time durations for each inspiration phase selected on the binary coding switch 170 will permit an expiration phase for the ventilator of at least 0.2 seconds, thereby ensuring that an infant to which the mouthpiece 34 is coupled has a safe period of time in which to exhale. If an expiration phase of at least 0.2 seconds is provided by the circuit portion 180 will remain quiescent; but if it is not, the portion 162 will signal the portion 174 on a line 180 to prevent activation of the solenoid 175 for a period of 5 seconds, and via a line 182 will signal an alarm portion of the circuitry enclosed by the dotted line 183 to activate the horn 184 and light a light-emitting diode 185 to alert an operator of the problem. After 5 seconds the circuit portion 162 will allow the portion 174 to activate the solenoid 175 to cause a single inspiration phase, but if the problem has not been corrected, will then again stop activation of the solenoid 175 via the portion 174 for another 5-second period, after which this sequence is repeated until the problem is corrected.

In addition to the circuitry of the alarm portion 183 described in the preceding paragraph, the alarm portion 183 of the control circuit also includes circuitry which will sound the horn 184 and light the light-emitting diode 186 when the switch 137 and solenoid 140 are activated by the overpressure safety system for the hose 30; circuitry that will sound the horn 184 and light the light-emitting diode 188 when the switch 116 is activated due to low gas pressure in the gas supply network 10; circuitry that will sound the horn 184 and light the light-emitting diode 189 when the switch 89 is activated due to an inspiration phase of over 3.5 seconds in duration; and circuitry that will light a light-emitting diode 190 as a pilot light when the main power to the ventilator is switched on. The alarm portion 183 also includes circuitry which will light a light-emitting diode 187 upon electrical power failure to the ventilator when it is turned on. The circuitry includes a battery 200 and a switch 201 which is operated in conjunction with a main on-off switch for the ventilator (not shown). Switching on the ventilator via the main switch closes the switch 201 to couple the battery 200 to circuitry that will apply the battery voltage to the light-emitting diode 187 if the main power fails. A push button test switch 202 is also provided to give the operator means for testing the electrical strength of the battery 200.

A suitable power supply (not shown) is also included in the control circuit to provide the indicated voltages at the various power input terminals.

Normally, the pneumatic and electrical components of FIGS. 1 and 2 will be mounted in a cabinet (not shown) except for the hose 30 and tube 126 which extend from the cabinet to an infant being ventilated; and the cabinet has a control panel on which the various light-emitting diodes, switches, control valves and other manually operated control devices described above are located.

The drawing filed with this application is informal and has the various component valves and nomenclature shown on the drawing. It is anticipated that when formal drawings are filed, the various components will be identified by reference numerals and the valves and nomenclature of the components will be shown in a table substituted for this paragraph.

It will be appreciated by those skilled in the art that many changes in the electronic and pneumatic circuitry could be made without departing from the spirit of the present invention. Thus the present invention should not be limited by the structure of the ventilator described above, but only by the structure described in the dependent claims and its equivalents.

We claim:
1. An infant ventilator comprising:
a gas delivery system including:
a supply portion comprising a first end adapted to be coupled to a source of gas under pressure, a second end, and a manually adjustable flow control valve between said first and second ends for regulating the rate of gas flow through said system;
a patient delivery portion having an inlet end coupled to the second end of said supply portion, an opposite outlet end, a mouthpiece between said inlet and outlet ends adapted to be coupled to the breathing passageways of an infant, means for restricting the flow of gas through said patient delivery portion to a rate in the range of about 0 to 25 liters per minute and for generating back-pressure at said second end of said supply portion, outlet valve means at said outlet end movable between a closed position to close the outlet end of said patient delivery portion and cause gas at said mouthpiece under sufficient pressure to cause involuntary inspiration of an infant to which said mouthpiece is coupled, and an open position so that gas will flow past said mouthpiece to allow exhalation of the infant, remove any exhaled gases from the mouthpiece and afford voluntary inhalation of the infant; and
a mouthpiece pressure-regulating portion, comprising a first end coupled to the second end of said supply portion, an opposite second end, venturi means coupled to said second end of said pressure-regulating portion and positioned in said patient delivery portion between said mouthpiece and said outlet valve means for lowering the gas pressure in said patient delivery portion adjacent said venturi means upon flow of gas from said pressure-regulating portion through said venturi means and said outlet valve means, and restriction means between the first and second ends of said mouthpiece pressure-regulating portion having a preset adjustment for regulating the gas flow through said venturi to rates that will cause generally the same pressure at said mouthpiece over said range of gas flow rates through said patient delivery portion; and
control means for switching said outlet valve means between its open and closed position in a predetermined timed sequence.

2. An infant ventilator according to claim 1 wherein said mouthpiece regulating means further includes means operated by said control means for interrupting gas flow to said venturi when said valve means is in said closed position.

3. A ventilator according to claim 1 or claim 2 further including means activated by a pressure at said mouthpiece above a predetermined valve for activating an alarm, exhausting said patient delivery portion, and interrupting the flow of gas through said supply portion.

* * * * *

UNITED STATES PATENT AND TRADEMARK OFFICE
CERTIFICATE OF CORRECTION

PATENT NO.   : 4,457,304

DATED        : July 3, 1984

INVENTOR(S)  : Hugo Molnar and David L. Robbins

Figure 2A:
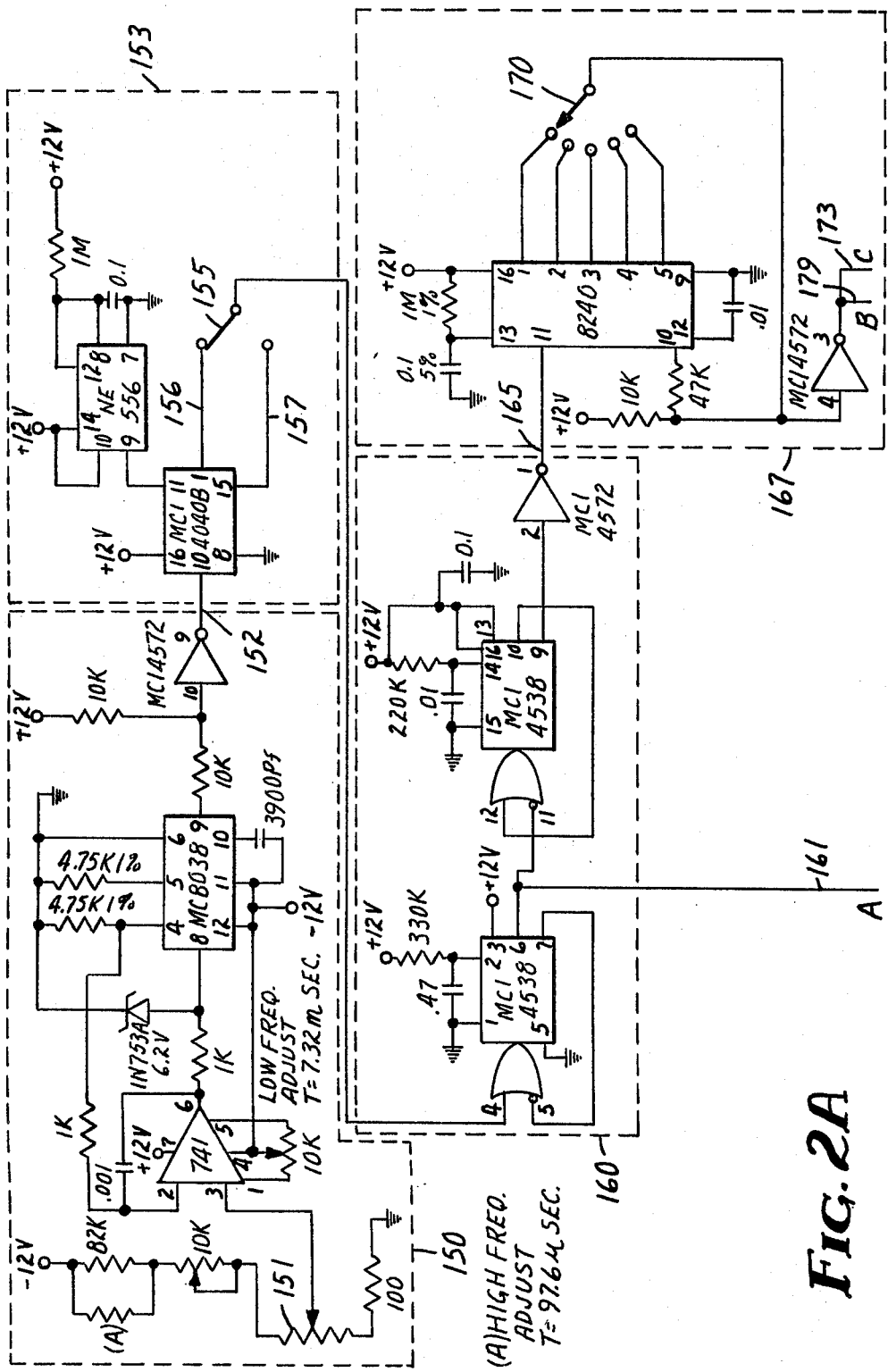
FIG. 2 is a schematic view of an electronic control circuit for controlling the gas delivery system of FIG. 1.
Figure 2B:
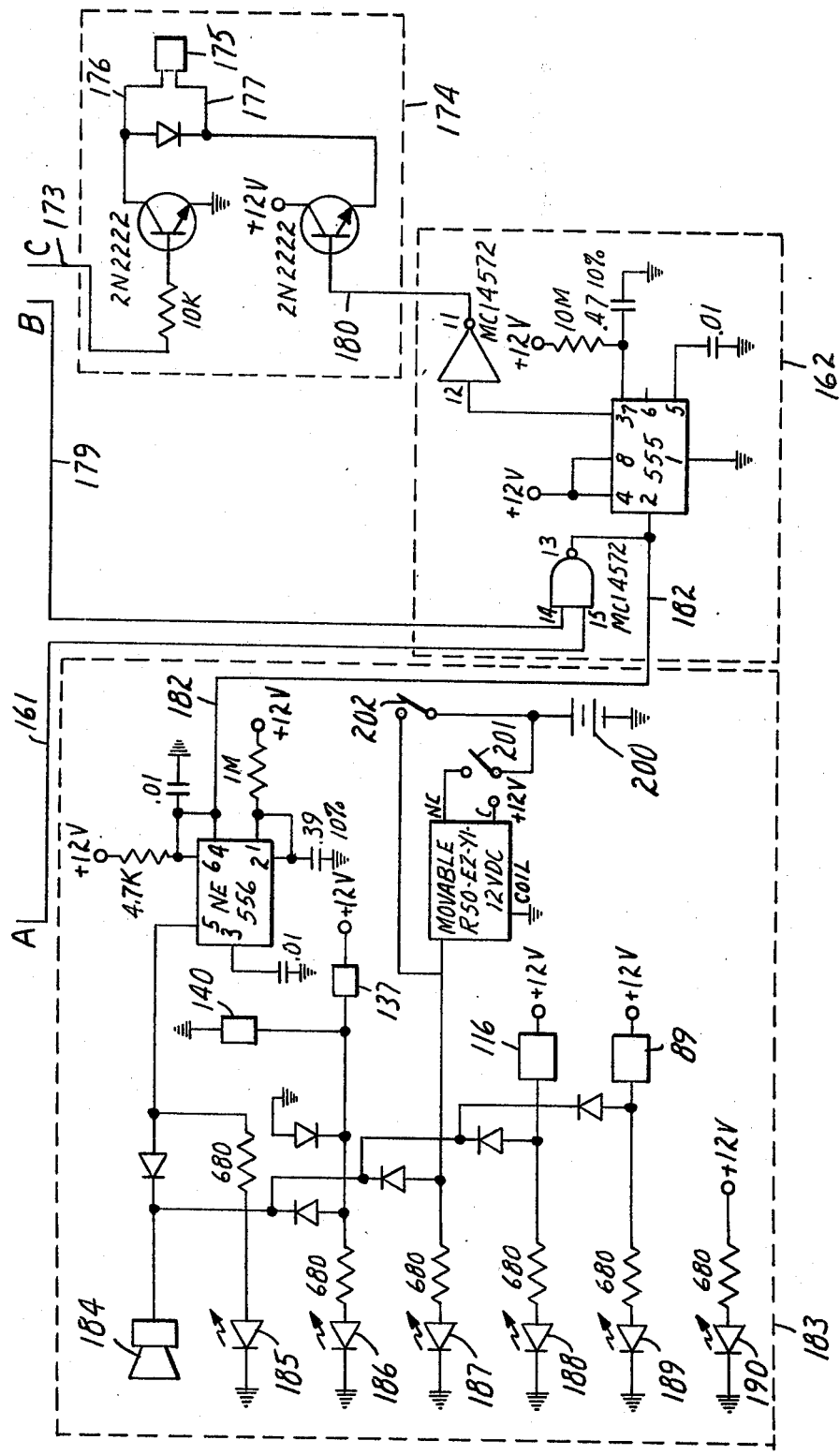

It is certified that error appears in the above-identified patent and that said Letters Patent is hereby corrected as shown below:

Col. 3, line 32 "Figure 2 is" should read --Figures 2A and 2B which together provide--.

Col. 4, line 45 after "spring" insert --return--.

Col. 4, line 47 "(Figure 2)" should read --(Figures 2A and 2B)--.

Col. 5, line 54 "pot" should read --port--.

Col. 5, line 59 "2" should read --2B--.

Col. 6, line 59 "(Figure 2)" should read --(Figures 2A and 2B)--.

Col. 7, line 41 "2" should read --2B--.

Col. 7, line 59 "(Figure 2)" should read --(Figures 2A and 2B)--.

Col. 8, line 27 "tha" should read --that--.

Col. 9, lines 33-39 should be deleted.

Signed and Sealed this
Twenty-third Day of December, 1986

Attest:

DONALD J. QUIGG

Attesting Officer        Commissioner of Patents and Trademarks